United States Patent
Brand et al.

(10) Patent No.: US 6,687,526 B2
(45) Date of Patent: Feb. 3, 2004

(54) METHOD FOR OPERATING A MAGNETIC RESONANCE APPARATUS HAVING AN ACTIVE SHIM SYSTEM

(75) Inventors: Martin Brand, Erlangen (DE); Rainer Kuth, Herzogenaurach (DE)

(73) Assignee: Siemens Aktiengesselschaft, Munich (GB)

(*) Notice: Subject to any disclaimer, the term of this patent is extended or adjusted under 35 U.S.C. 154(b) by 273 days.

(21) Appl. No.: 09/884,653

(22) Filed: Jun. 19, 2001

(65) Prior Publication Data

US 2001/0053877 A1 Dec. 20, 2001

(30) Foreign Application Priority Data

Jun. 20, 2000 (DE) .......................................... 100 30 142

(51) Int. Cl.⁷ ................................................. A61B 5/05
(52) U.S. Cl. ........................ 600/410; 600/411; 324/320; 335/301
(58) Field of Search ................................. 600/410, 411, 600/420, 424, 425; 324/307, 309, 318, 319, 320, 322; 335/301, 299

(56) References Cited

U.S. PATENT DOCUMENTS

| | | | |
|---|---|---|---|
| 4,899,109 A | * | 2/1990 | Tropp et al. ................. 324/320 |
| 5,391,990 A | | 2/1995 | Schmitt et al. |
| 5,490,509 A | | 2/1996 | Carlson et al. |
| 5,614,827 A | | 3/1997 | Heid |
| 6,023,167 A | * | 2/2000 | DeMeester et al. .......... 324/318 |
| 6,064,208 A | * | 5/2000 | Steckner ...................... 324/320 |
| 6,294,972 B1 | * | 9/2001 | Jesmanowicz et al. ....... 335/301 |

* cited by examiner

Primary Examiner—Quang T. Van
(74) Attorney, Agent, or Firm—Schiff Hardin & Waite

(57) ABSTRACT

In a method for operating a magnetic resonance apparatus with a gradient coil system and an active shim system, shim currents of the active shim system and/or offset currents of the gradient coil system are adjusted corresponding to at least one subject-specific parameter of an examination subject.

15 Claims, 1 Drawing Sheet

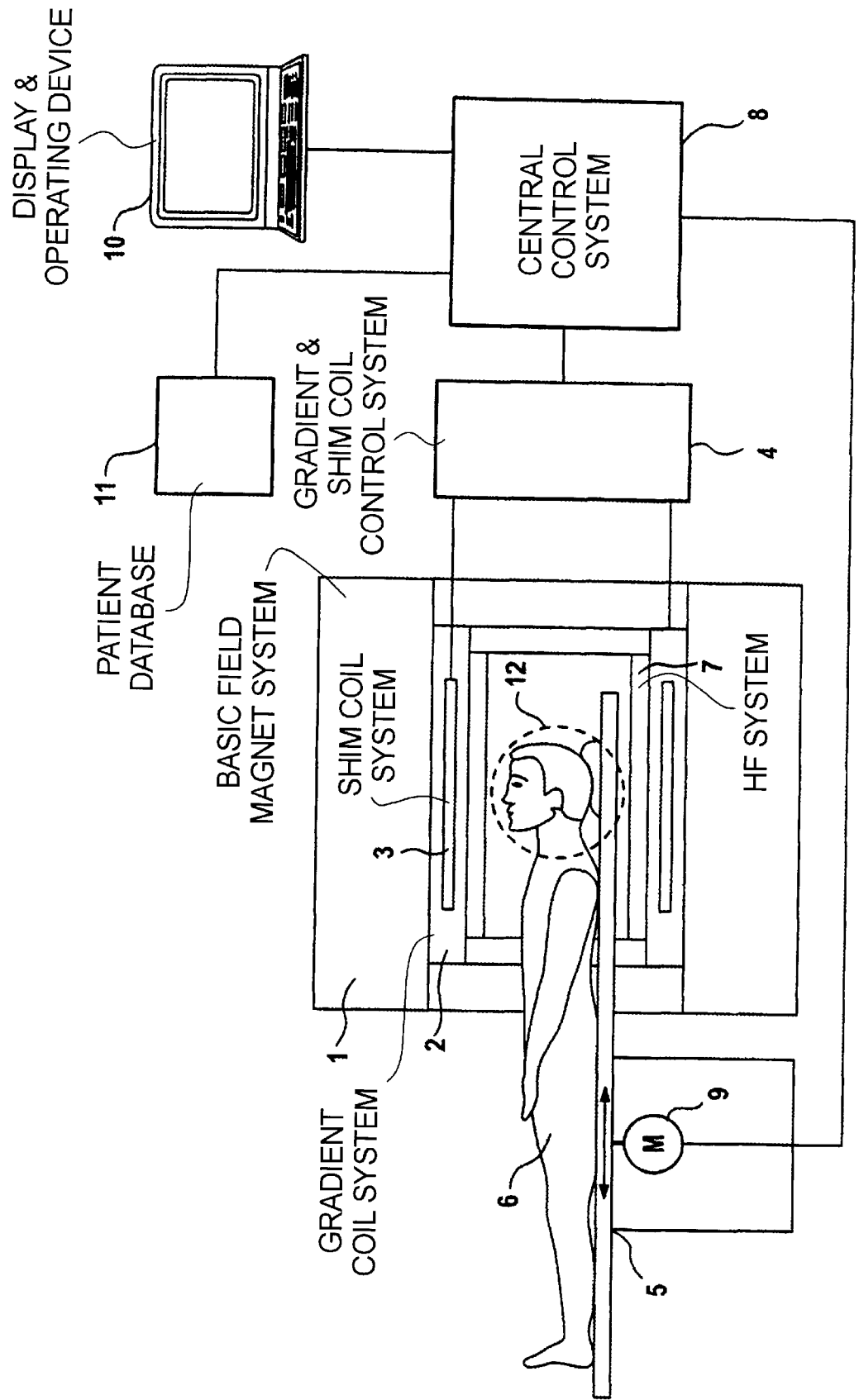

METHOD FOR OPERATING A MAGNETIC RESONANCE APPARATUS HAVING AN ACTIVE SHIM SYSTEM

BACKGROUND OF THE INVENTION

1. Field of the Invention

The present invention relates to a method for operating a magnetic resonance apparatus having a gradient coil system and an active shim system.

2. Description of the Prior Art

Magnetic resonance imaging is a known technique for acquiring images of the inside of a body of an examination subject. In a magnetic resonance apparatus, rapidly switched gradient fields that are generated by a gradient system are superimposed on a static basic magnetic field, which is generated by a basic field magnet system. The magnetic resonance apparatus also has a high-frequency system, which emits high-frequency signals into the examination subject for triggering magnetic resonance signals, and which receives the generated magnetic resonance signals, on the basis of which image datasets are prepared.

In magnetic resonance imaging, sufficient homogeneity of the basic magnetic field constitutes a determining factor for the quality of the magnetic resonance images. Non-homogeneity of the basic magnetic field, within an imaging volume of the apparatus, causes geometric distortions of the magnetic resonance image, which is proportional to the field non-homogeneity. The field homogeneity is particularly important for rapid pulse sequences, for example in the echoplanar method.

It is known to employ shim systems for improving the basic magnetic field homogeneity within the imaging volume. A distinction is made between passive shim systems and active shim systems. In a passive shim system, a number of iron sheets or plates are attached with a suitable arrangement in the examination space of the apparatus. For this purpose, the basic magnetic field is measured within the imaging volume prior to the attachment of the iron plates. From the measured values, a calculating program determines the appropriate number and arrangement of the iron plates.

In an active shim system, shim coils that can be charged with direct current are used for homogenizing the basic magnetic field. Power packs supplying very constant and reproducibly adjustable direct currents are necessary for operating the shim coils. Among other things, an active shim system is used for precision correction when extremely high homogeneity is important, for example for correcting field distortions caused by the susceptibility of the examination subject, who is at least partially situated in the imaging volume.

For example, as is known from the German Patent 195 11 791 C1, the basic magnetic field can be described within the imaging volume with coefficients of a spherical function series expansion. It is also known from the aforementioned German Patent to correct linear non-homogeneity of the basic magnetic field, i.e., a field disturbance of first order, by charging a gradient coil with an offset current. The offset current is a constant current, which is superimposed on the gradient coil current used in a gradient sequence. In order to compensate field non-homogeneity of higher order, respective shim coils essentially compensating different ones of the coefficients are provided, corresponding to the field disturbance to be compensated. Nine shim coils generally are sufficient even high for homogeneity requirements, so that, together with the three gradient coils, twelve coefficients representing the primary disturbances to the field homogeneity can be brought close to zero.

Due to the basic magnetic field-distorting effect of the examination subject, a shim adjusting process is carried out in the course of preparing magnetic resonance images. Shim currents are determined for the individual shim coils and offset currents are determined for the gradient coils after a region of the examination subject to be imaged has been positioned in the imaging volume. Corresponding to the aforementioned German Patent, magnetic resonance signals of the examination subject are generated with different echo times for forming two three-dimensionally spatially resolved raw datasets, and the raw datasets are further processed for determining corresponding shim currents and offset currents.

German OS 42 27 162 discloses an iterative method for adjusting the shim currents and offset currents. For this purpose, proceeding from an initial adjustment of the shim currents and offset currents, magnetic resonance signals of the examination subject are generated, which are subjected to a correlation process for determining an improved adjustment of the shim and offset currents. With the thus-determined improved adjustment of the shim currents and offset currents, the aforementioned method step is repeated until a sufficient basic filed homogeneity is obtained.

U.S. Pat. No. 5,490,509, for a magnetic resonance apparatus, discloses an active shim system fashioned as an electromagnet, whereby the shape of the imaging volume of the magnetic resonance apparatus can be chronologically varied by correspondingly driving the shim system. In this way, a magnetic resonance image can be picked up from an ellipsoid-shaped imaging volume which is extended in one direction, for example for picking up a longer region of a spine, instead of being picked up from an essentially spherical imaging volume.

In the previously described shim adjusting method, which is based on a measurement and evaluation of magnetic resonance signals of an examination subject, it is particularly disadvantageous that a time duration of approximately one minute must be expected per examination. Among other things, this has a negative effect on achieving a high patient throughput for a magnetic resonance device.

SUMMARY OF THE INVENTION

An object of the invention is to provide an improved method of the aforementioned type with which, among other things, a fast shim adjusting process can be carried out.

This object is achieved in accordance with the invention by adjusting the shim currents of the active shim system and/or offset currents of the gradient coil system corresponding to at least one subject-specific parameter of an examination subject. As a result, a time-intensive measurement and evaluation of the shim currents and offset currents for adjusting the shim currents and offset currents can be foregone. Thus, a higher patient throughput can be obtained. Furthermore, an improved quality of the magnetic resonance images can be achieved in examinations, wherein—for whatever reasons—a shim adjusting process as described in the prior art has not been carried out by using the inventive method, without the shim adjusting process adding any significant time delay.

In an embodiment, the subject-specific parameter is the mass, length, gender and/or age of the examination subject. Mass, length, gender and age of the examination subject to a large extent determine the examination subject-dependent field-distorting effect.

In another embodiment, shim currents and/or offset currents are adjusted dependent on at least one execution-specific parameter of an examination. For this purpose, the execution-specific parameter is an indication of an area of the examination subject to be imaged and/or the orientation of the area with respect to the magnetic resonance apparatus. For this purpose, the indication and/or orientation of the area to be imaged, in an embodiment, is determined from a travel or: movement position of a movable support device of the magnetic resonance apparatus, the type of supporting arrangement of the examination subject on the support device and/or from a use of a local reception antenna. For adjusting the shim currents and offset currents, it is important to know the area to be imaged within an examination subject, this area being situated in the imaging volume of the apparatus. For a patient, the use of a local head antenna, for example, indicates that the area of the patient to be imaged is the head. By knowing the movement position of the support device, the area of the patient to be imaged can also be determined from the support type of the patient on the support device, such as lying on the stomach or back, with the head or legs in front.

In a further embodiment, the parameters are obtained from input data of the magnetic resonance apparatus. For example, an input designating the patient's mass must be entered into the magnetic resonance apparatus, in any event so that the SAR (Specific Absorption Rate) to limit the high-frequency performance.

In a further embodiment, the parameters are obtained from a patient database. The data stored in the patient database are immediately available to the magnetic resonance apparatus when the magnetic resonance apparatus is correspondingly linked with a patient database in which the length of a patient is stored, for example.

In a further embodiment, shim currents and/or offset currents are allocated to a combination of parameters by a selection from a table. A table is generated, for example in the framework of a series of tests with examination subjects of different length and mass, by determining optimal adjustments of the shim currents and offset currents on the basis of measuring techniques, for example according to one of the previously cited methods.

In another embodiment, a neural network determines suitable shim currents and/or offset currents for a combination of parameters. The neural network is supplied with inputs in order to obtain a sufficiently long learning phase having a sufficiently large number of shim currents and/or offset currents, which are determined on the basis of a measuring technique. From an input of the subject-specific and execution-specific parameters, adjustment for shim currents and offset currents, can be determined on the basis of a measuring technique with a method according to the aforementioned German Patent. For example, a magnetic resonance apparatus can be fashioned with which shim currents and offset currents either can be adjusted by the neural network or by a measuring-oriented method. Given a deficient shim adjustment by the neural network, for example as a result of an extraordinarily massive examination subject, a suitable adjustment is determined on the basis of the measuring-oriented method. It is used for generating magnetic resonance images and simultaneously is fed, with all parameters of the examination subject, to the neural network for learning. The above description for a neural network is applicable for a table replacing the neural network. Adjustments that are determined on the basis of a measuring technique correspondingly expand the table.

DESCRIPTION OF THE DRAWINGS

The single FIGURE is a schematic block diagram of a magnetic resonance apparatus operating in accordance with the principles of the present invention.

DESCRIPTION OF THE PREFERRED EMBODIMENTS

The FIGURE shows a magnetic resonance device having a basic field magnet system 1 for generating a basic magnetic field and a gradient coil system 2 for generating gradient fields. A shim coil system 3 is integrated into the gradient coil system 2 for homogenizing the basic magnetic field. The gradient coil system 2 and the shim coil system 3 are connected to a gradient and shim control system 4 in order to control currents in the gradient coil system 2 and in the shim coil system 3. Moreover, the apparatus has a movable support device 5 on which a patient 6 to be examined is borne. The apparatus also has a high-frequency system 7, which emits high-frequency signals into the patient 6 for triggering magnetic resonance signals and which receives the generated magnetic resonance signals.

For the coordinated operation of the magnetic resonance apparatus, the apparatus has a central control system 8 that is connected to the gradient and shim control system 4. In order to control a motion of the movable support device 5, the central control system 8 is correspondingly connected to a driving device 9 of the movable support device 5. Furthermore, the central control system 8 is connected to a display and operating device 10 via which inputs of the user are supplied to the central control system 8, and at which magnetic resonance images are displayed. The central control system 8 of the device is coupled with a patient database 11, so that patient data, such as length, gender and age of the patient 6, are retrievable for the central control system 8.

At the beginning of a magnetic resonance examination, the patient 6 is borne on the support device 5, which extends out of the basic magnetic field 1 as far as possible. The patient 6 is supported in a manner that is dependent on an area to be imaged, which is fixed at the start of the examination. If the head of the patient 6 is the area to be imaged, the patient 6 is positioned on the support device 5 having his or her head in front. If the legs of the patient 6 are to be examined, the patient is positioned on the support device 5 having his or her legs in front. Depending on diagnostic requirements, it can also be selected whether the patient 6 is supported on the back or on the stomach. The manner of support of the patient 6 is correspondingly indicated at the display and operating device 10. The mass of the patient 6 is also entered in order to limit the high-frequency performance during the examination, which is dependent on the mass of the patient. For the actual examination, the support device 5 is moved such that the selected area to be imaged is positioned in the imaging volume 12 of the device.

Knowing the area to be imaged and its orientation with respect to the magnetic resonance apparatus, a corresponding shim current and offset current adjustment is determined and executed, in connection with the mass, the length, the gender and/or the age of the patient 6, by accessing a table stored in the central control system 8. Patient-specific parameters, such as mass, length, gender and/or age, and corresponding adjustments for shim currents and offset currents, are stored in the table for different combinations from areas to be imaged and their orientation. The area to be imaged and its orientation are calculated in the central control system 8 from a travel position of the support device 5, the supporting manner of the patient 6 on the support device 5, and the length of the patient 6. The shim adjustment ensues without a delay. A time-involved measuring and evaluating of magnetic resonance signals in order to adjust shim currents and offset currents is not necessary.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a magnetic resonance apparatus having a gradient coil system and an active shim system and an imaging volume adapted to receive a portion of an examination subject, said method comprising the steps of:

without conducting a magnetic resonance examination of said examination subject, identifying at least one subject-specific parameter of said examination subject; and adjusting at least one current, selected from the group consisting of shim currents of said active shim system and offset currents of said gradient coil system, dependent on said at least one subject-specific parameter for obtaining a selected homogeneity within said imaging volume for a subsequent magnetic resonance examination using said magnetic resonance apparatus with said portion of said examination subject received in said imaging volume.

2. A method as claimed in claim 1 comprising selecting said subject-specific parameter from the group consisting of mass and length of said examination subject.

3. A method as claimed in claim 1 comprising selecting said subject-specific parameter from the group consisting of gender and age of said examination subject.

4. A method as claimed in claim 1 comprising additionally adjusting said at least one current dependent on at least one execution-specific parameter of said subsequent examination conducted using said magnetic resonance apparatus.

5. A method as claimed in claim 4 wherein said execution-specific parameter identifies said portion to be imaged of said examination subject.

6. A method as claimed in claim 4 wherein said execution-specific parameter identifies an orientation, relative to said magnetic resonance apparatus, of said portion to be imaged of said examination subject.

7. A method as claimed in claim 4 comprising selecting said execution-specific parameter from the group consisting of an identification of said portion to be imaged of said examination subject and an orientation, relative to said magnetic resonance apparatus, of said portion to be imaged of said examination subject, and wherein said magnetic resonance apparatus includes a movable patient support device for moving said examination subject in said magnetic resonance apparatus relative to said imaging volume, and comprising the step of determining said execution-specific parameter from a movement position of said patient support device.

8. A method as claimed in claim 4 comprising selecting said execution-specific parameter from the group consisting of an identification of said portion to be imaged of said examination subject and an orientation, relative to said magnetic resonance apparatus, of said portion to be imaged of said examination subject, and wherein said magnetic resonance apparatus includes a movable patient support device for moving said examination subject in said magnetic resonance apparatus relative to said imaging volume, and comprising the step of determining said execution-specific parameter from a manner by which said examination subject is supported on said patient support device.

9. A method as claimed in claim 4 wherein said execution-specific parameter is selected from the group consisting of an identification of said portion to be imaged of said examination subject and an orientation, relative to said magnetic resonance apparatus, of said portion to be image of said examination subject, and wherein said magnetic resonance apparatus includes a local reception antenna, and wherein said execution-specific parameter is identified dependent on said local reception antenna.

10. A method as claimed in claim 1 comprising the additional step of entering input data into said magnetic resonance apparatus for conducting said subsequent examination of said examination subject, including obtaining an image of said portion of said examination subject in said imaging volume, and comprising deriving said at least one subject-specific parameter from said input data.

11. A method as claimed in claim 1 comprising compiling a patient data base and selecting said at least one patient-specific parameter from said patient data base.

12. A method as claimed in claim 1 comprising compiling a table containing a plurality of combinations of different patient-specific parameters with different values of said at least one current being respectively allocated to said combinations, and selecting one of said values for said at least one current from said table.

13. A method as claimed in claim 1 comprising determining said at least one current from a plurality of patient-specific parameters in a neural network.

14. A method as claimed in claim 13 comprising feeding said neural network with said plurality of patient-specific parameters in a learning phase for developing a plurality of values, for different combinations of said parameters, for said at least one current.

15. A method as claimed in claim 1 comprising adjusting said at least one current repeatedly in an iterative procedure With an evaluation of magnetic resonance signals obtained from said portion of said examination subject in said volume in each iteration.

* * * * *